United States Patent

Björk et al.

Patent Number: 4,492,698
Date of Patent: Jan. 8, 1985

[54] DIPHENYLBUTYL-1-ACYLPIPERAZINES

[76] Inventors: Anders K. Björk, Svalvägen 9; Aina L. Abramo, Järavallsgatan 30, both of S-230 50 Bjärred; Erik G. Christensson, Nils Bjelkegatan 3 A, S-222 20 Lund, all of Sweden

[21] Appl. No.: 354,088

[22] PCT Filed: Jun. 5, 1981

[86] PCT No.: PCT/SE81/00169
§ 371 Date: Jan. 25, 1982
§ 102(e) Date: Jan. 25, 1982

[87] PCT Pub. No.: WO81/03658
PCT Pub. Date: Dec. 24, 1981

[30] Foreign Application Priority Data

Jun. 16, 1980 [SE] Sweden .................. 8004465

[51] Int. Cl.³ .................. A61K 31/495; C07D 241/04
[52] U.S. Cl. .................. 424/250; 544/377; 544/386; 544/379; 544/391
[58] Field of Search .................. 544/391, 377; 424/250

[56] References Cited

U.S. PATENT DOCUMENTS

| | | | |
|---|---|---|---|
| 2,742,472 | 4/1956 | Baltzly et al. | 544/391 |
| 2,794,804 | 6/1957 | Kushner et al. | 544/391 |
| 4,080,453 | 3/1978 | Nishimura et al. | 544/391 |
| 4,265,894 | 5/1981 | Gootjes | 544/391 |
| 4,308,387 | 12/1981 | Björk | 424/250 |

FOREIGN PATENT DOCUMENTS 50-151885  12/1975  Japan .................. 544/391

OTHER PUBLICATIONS

Björk, et al., "Chemical Abstracts", vol. 99, 1983, Col. 99:158462f.

*Primary Examiner*—Glennon H. Hollrah
*Assistant Examiner*—James H. Turnipseed
*Attorney, Agent, or Firm*—Scully, Scott, Murphy & Presser

[57] ABSTRACT

Novel compounds of the formula

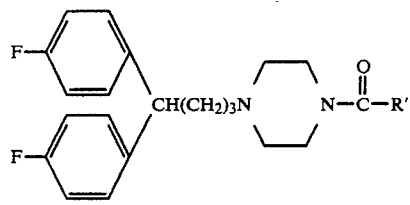

wherein R' is selected from the group consisting of alkyl straight or branch chained having from 2 to 10 carbon atoms, cycloalkyl having from 3 to 8 carbon atoms, aralkyl having from 7 to 9 carbon atoms, phenyl and substituted phenyl wherein the substituents of the substituted phenyl are selected from the group consisting of one to three F, Cl, Br, lower alkyl having from 1 to 5 carbon atoms, lower alkoxy having from 1 to 5 carbon atoms, alkylenedioxy having from 1 to 3 carbon atoms, —$CF_3$ and —CN and pharmaceutically acceptable salts thereof which have been found to have utility for therapeutic treatment of mental disorders by reducing anti-aggressive behavior and a process for making the compounds.

9 Claims, No Drawings

DIPHENYLBUTYL-1-ACYLPIPERAZINES

FIELD OF INVENTION

The present invention relates to novel diphenylbutyl-1-acylpiperazines and their acid addition salts having pharmacologically valuable properties, processes for the preparation thereof and therapeutic compositions containing said compounds.

PRIOR ART

French Pat. No. 2,367,067 (CA 89: 24362 h) describes as having analgetic properties piperazine derivatives of formula:

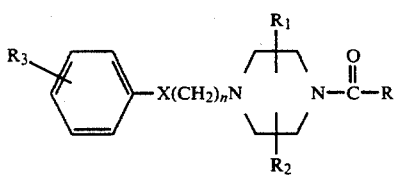

wherein R represents a lower unsaturated alkyl or furyl group or a lower alkyl group optional substituted by a lower alkoxy group, $R_1$ and $R_2$ represent a methyl or ethyl group, $R_3$ represents a hydrogen atom or a methyl or a methoxy or a hydroxy group, X is O, CO, $CO_2$, $CR_4R_5$ or $NCOR_6$, $R_4$ represents a hydrogen atom or a lower alkoxy or a lower acyloxy or a hydroxy group, $R_5$ represents a hydrogen atom or a phenyl group, $R_6$ represents a lower alkyl group and n is 1, 2 or 3.

In the article "In vitro Metabolism of Lidoflazine by Rat and Dog Liver Fractions" by W. Meuldermans et al in Arzneim.-Forsch./Drug Res. 27 (I) 832 (1977) the compound 1-acetyl-4-[4,4-(di-fluorophenyl)butyl]piperazine is incidentally shown as a Lidoflazine metabolite among a number of other metabolites in a scheme illustrating metabolic pathways of lidoflazine. However, said compound is only shown by means a formula and there are no statements at all concerning any properties of the compound.

DESCRIPTION OF THE INVENTION

It has now been found that compounds of formula I:

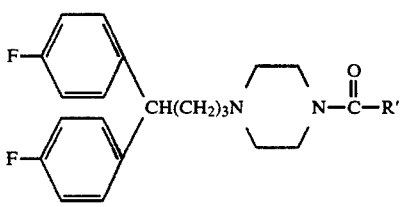

wherein R' is alkyl straight or branch chained having from 2 to 10 carbon atoms, preferably 2-3 carbon atoms, cycloalkyl having from 3 to 8 carbon atoms, preferably 3 carbon atoms, aralkyl having from 7 to 9 carbon atoms or phenyl unsubstituted or substituted by one to three F, Cl, Br, lower alkyl having from 1 to 5 carbon atoms, lower alkoxy having from 1 to 5 carbon atoms, alkylenedioxy having from 1 to 3 carbon atoms, —$CF_3$ or —CN substituents and their pharmaceutically acceptable salts unexpectedly exhibit valuable antiaggressive, antipsychotic and antidepressive properties.

Furthermore, the compounds of formula I exhibit very potent analgetic properties.

Among the compounds A described in the above mentioned French patent specification No. 2,367,067, which have been found to possess analgetic properties, the compound which is most closely related to the compounds according to the present invention is the compound wherein R=ethyl, $R_1=R_2$=methyl, X=CH-Ph, $R_3$=H, n=2, which hereinafter is referred to as compound $A_1$. However, said compound $A_1$ differs chemically in several respects from the compounds according to the present invention. Thus, the known compound $A_1$ have no fluorine substituents in the two benzene rings and furthermore, the known compound has methyl substituents in positions 2 and 5 of the piperazine ring which is not the case for the compounds according to the present invention. Fluorine substitution in the para position of the benzene rings and hydrogen substitution in positions 2 and 5 of the piperazine ring of the known compound $A_1$ carried out separately or in combination in all cases substantially reduce the potency relative to compound $A_1$. However, it has according to the present invention surprisingly been found that lengthening of the side-chain together with fluorine substitution in the para position of the benzene rings and the absence of any C-substitution in the piperazine ring, i.e. the compound of Formula I according to the present invention wherein R'=ethyl, leads to a tenfold increase in potency and prolonged activity relative to compound $A_1$. This demonstrates the important and unexpected improvements obtained by means of the compounds I according to the present invention as compared to the most closely related prior art.

As already is pointed out above the cited article of Meuldermans et al only by means of a formula shows the compound 1-acetyl-4-[4,4-(di-fluorophenyl)butyl]-piperazine, hereinafter referred to as compound B, as a metabolite among other metabolites in a scheme. The article contains no statements as to any properties of said compound. However, as will be shown in the tests of pharmacological properties described in the present application said compound B is inferior to the compounds I of the present invention.

There is much evidence that psychopharmacology has been moving in circles in the search for new antipsychotic, antidepressant and antianxiety drugs ever since systemic methods of pharmacological screening of such drugs in animals were introduced. Drugs that were predicted to possess specific psychotrophic properties on basis of their pharmacological resemblance to a traditional type of drug have in the clinical failed to be more effective than existing drugs. With regards to neuroleptics, the search for cataleptic properties as well as for antagonism of amphetamine and apomorphine induced stereotypies have preserved extrapyramidal side-effects in all drugs of this type hitherto developed.

Until recently the therapeutic efficacy of the neuroleptics was considered to be closely associated with the extra pyramidal motor action and was evaluated in terms of their ability to produce a characteristic catalepsy in animals. It is however now believed that the extrapyramidal dysfunction is caused by blockage of the dopamine receptors in the striatum (Hornykiewicz, O. in Handbook of Neurochemistry, Lajtha, A. ed. Plenum Press New York 1973 p. 465) whereas the antipsycotic activity is due to a similar interaction in the mesolimbic area of the brain (Anden, N. E. et al J. Pharm.Pharmacol., 25, 346 (1973); Bertholini, G. ibid. 28 429 (1976)).

Neither cataleptogenic properties nor antagonism of amphetamine or apomorphine induced stereotypies in animals are of any value as predictors for antipsychotic potency by the drug in patients in the clinic. There is also a need for better antidepressants with fewer and less severe side effects, especially the cardiotoxic ones. The therapeutic effectiveness is still far from ideal. Still, in most cases electroconvulsive treatment is more effective than any antidepressant drug known today. Instead of present antidepressants having a therapeutic effectiveness in 65–75% of the patients one ought to pursue the goal that future antidepressants be effective in more than 90% of the patients. Furthermore, recent antianxiety drugs are not truly specific. Beside relief of excessive anxiety and tension these drugs produce side effects such as drowsiness, decrease of alertness and disturbed psychomotor performance. A very pronounced drawback of the new drugs is the tendency to create tolerance or physical dependence. Many times they have synergistic action when combined with a alcohol or other depressant drugs.

The compound presented in this invention constituting a new prototype will be useful in the treatment of mental disorders or diseases in the peripheral nerve system based on the same mechanism of action as the mental disorders. The term "treatment of mental disorders" is meant to include administration of the compounds of formula I to a patient who has already been identified to suffer from psychotic disorders and personality disorders. (van Praag, H. M., in The Neurobiology of Dopamine, Horn, A. S. et al., Ed., Academic Press, 1979, p. 655). Contrary to classical neuroleptics and antianxiety drugs, the compounds of formula I have a balanced activating potency and they should therefore be useful as antidepressants. The compounds are also capable of relieving both physical and emotional pain.

The compound of formula I have a new pharmacological profile not seen in any compound described earlier. The compounds produce longlasting inhibition of aggressive behaviour without causing any sedation, catalepsy or ataxia. In contrast to typical neuroleptics the compounds do not antagonize the stereotypy induced in rats by amphetamine or apomorphine. These pharmacological properties mean that the compounds should not induce any acute extrapyramidal side effects or tardive dyskinesia on chronic administration. Furthermore, the compounds should not interfere with alertness, mental performance or coordination of movements, which are of importance in out-patients (patients not staying in hospitals). The compounds block condition avoidance response (CAR) and exploratory behaviour only at high doses. The potent activity in aggression tests, the effects on cognitive and integrative processes as well as inhibition of [$^3$H]-spiroperidol binding in defined parts of the brain are suggestive of future usefulness in psychotic conditions. The compounds show very potent analgetic properties, which are not reversed by naloxone.

The analgetic properties of the compounds, the lack of effect on consciousness and the lack of being hypnotic or addictive imply that the compounds should be very useful in the treatment of chronic pain in different diseases and also of acute pain in connection with operations as well as in painful examinations. The analgetic and anti-inflammatory effects of the compounds, the effect on the immunologic system as well as the psychotropic effect are suggestive of their future usefulness in geriatric and rheumatoid patients.

The antianxiety effect and the protecting effect on induced stress in animals exhibited by the compounds will be of value in the treatment of depressive illnesses and also of psychosomatic disorders such as ulcus in man.

The new compounds are very useful in the treatment of aggressive behaviour in animals, especially in pigs, and also in promoting the development of a natural hierarchy in groups of animals without bursts of aggression and in calming of anxious and stressed animals.

The compounds have no or very few autonomical side effects and a low degree of toxicity.

According to further features of the present invention there are provided the following processes for the preparation of the novel acylpiperazines of formula I:

A(a) by reacting a 1-acylpiperazine of formula II

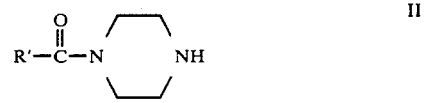

with a 4-substituted 1,1-diarylbutane of formula III

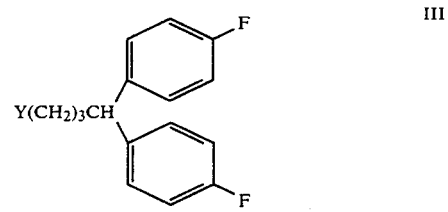

wherein R' is as above defined and Y is halogen, preferably Br or another reactive group, e.g. a mesyl or tosyl ester group, to form a compound of formula I.

A(b) by reacting a 1-(4,4-diaryl-butyl)piperazine of formula IV

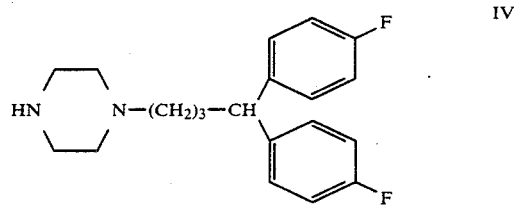

with an acyl chloride R'-COCl to form a compound of formula I.

The 1-acylpiperazines of formula II employed in the processes according to the invention may be prepared by a sequence of operations starting with:

B(a) a reaction between an acyl chloride R'-COCl and a 1-benzyl-piperazine of formula V

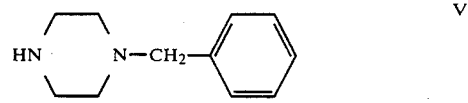

in chloroform or the like to form a compound of formula VI

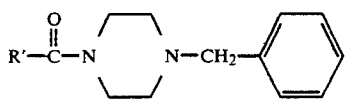

The compound of formula VI is hydrogenated over a noble metal catalyst to give the compound of formula II.

In sequence A(a) the compound of formula II is reacted with a compound of formula III (synthesised according to French Patent M 3695) in a suitable solvent, e.g. a lower alkanol, such as methanol, ethanol, n-butanol and the like, in the presence of an acid acceptor, i.e. an appropriate base, e.g. an alkali metal carbonate or bicarbonate, which may be utilised to bind the acid that is liberated during the course of the reaction to give the compound of formula I. Elevated temperatures may be employed to enhance the rate of reaction.

In sequence A(b) the compound of formula IV (synthesised according to Neth. Appln. No. 6,507,312) is reacted with an acyl chloride R'-COCl in a suitable solvent, e.g. diethyl ether, chloroform, toluene and the like to form the compounds of formula I. The mixture is reacted over a wide range of temperatures from about 10° C. to about 110° C., although it is possible to employ temperatures above and below this range.

The writhing test is a frequently used test of analgetic properties (Witkin, L. B. et al., J. Pharmacol. Exp. Ther. 133, 400 (1961)). If acetic acid (0.5%, 15 ml/kg) is injected intraperitoneally in mice (NMRI) they will without exception develop a writhing behaviour characterized by stretching their hind legs. The drugs to be tested were administered subcutaneously to 6 female mice at each dose 20 min. before the injection of the acetic acid. After 10 min. The behaviour of the mice was studied in 5 min. The $ED_{50}$ value is the dose blocking the writhing behaviour in 50% of the animals during the 5 min. study period.

Male mice subjected to prolonged isolation develop aggressive behaviour against each other when paired (Yen, C. Y. et al., Arch. Int. Pharmacodyn. 123, 179, (1959); Valzelli, L., Adv. Pharmacol. 5, 79 (1967)). All clinically used neuroleptics and antidepressants studied in this test inhibit this aggressive behaviour although their activity may differ. Also anxiolytic drugs, e.g. diazepam, are active on this kind of aggressive behaviour. The clinical correlation of this test indicates tranquillizing and anxiolytic activities as well as antiaggressive properties as such (Duncan, R. L. et al., J. Med. Chem. 13, 1 (1970)).

This type of aggression is interesting because it is known that this kind of emotional behaviour might be located in limbic structures in the brain (MacLean, P. D., Psychosom. Med. 11, 338 (1949)).

Every week male NMRI mice, weighing 20-22 g, were isolated in Makrolon cages for three weeks with diet and water ad libitum. A piece of cardboard was placed between the cages to prevent visual contact.

To test aggressiveness the mice were paired in a neutral area, a beaker (14 cm high and diameter 14 cm). A pair is considered aggressive if both the animals show clear signs of fighting within 5 min. This fighting is characterized by biting and vocalization. As soon as fighting is seen, the mice are separated and brought to their home cage. (Every second mouse is marked.) If only one of two mice exhibit aggressive behaviour the aggressive one is paired with another to make a well matched, aggressive pair. Animals showing no aggression are discarded. The frequency of paired mice exhibiting fighting varies from 5-100 percent depending on the time of the year. The test substance is administered s.c. (0.2-0.4 ml/20 g). The mice are paired 0.5 h after the injection for trials of 5 min. duration.

The $ED_{50}$-value (mg/kg) reported is the dose inhibiting aggressive behaviour among 50 percent of the pairs 0.5 hour after drug administration.

For the purpose of detecting new psychotropic substances with antiaggressive properties, pharmacologist have used several different models. One model used, the mouse-killing (muricide) by rats (Vogel, J. R. in Industrial Pharmacology, Vol. 2, Antidepressants, Stuart, F. and Lal, H., Ed., Futura Publishing Company, 1975, p. 99), is based on an existing interspecies aggression (Karli, P., Behaviour 10, 81 (1956)). This form of aggressive behaviour which is considered to be of predatory nature, is physiologically and topographically different from other forms of aggression (O'Boyle, M., Psychol. Bull. 81, 261 (1974)). Mousekilling is a spontaneous behaviour in some rat strains e.g. male hooded Long-Evans rats.

Male hooded Long-Evans rats placed in individual cages were used. By testing a number of rats, a colony of rats was obtained that killed a mouse whenever introduced into the rats' cage, by biting the mouse through the cervical spinal cord.

Each rat was tested for mouse-killing behaviour (killing a mouse within 5 minutes) prior to each experiment, thus serving as its own positive control. For each dose level 6 positive rats were selected and the test substance was administered by subcutaneous injection. Doses were selected to form a dose-response curve and the mean effective dose ($ED_{50}$, mg/kg) was calculated by means of linear regression. The rats were tested at 1, and 2 hours after being injected subcutaneously.

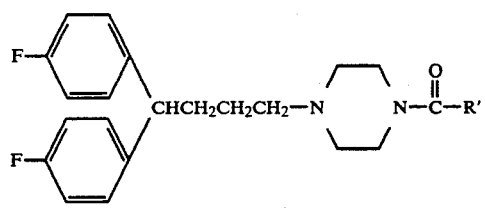

TABLE 1

| | Analgetic properties | |
|---|---|---|
| Compound | R' | $ED_{50}$, mg/kg, s.c. |
| 1 | Et | 0.5 |
| 2 | iso-Pr | 1.1 |
| 3 | cyclo-Pr | 0.8 |
| $A_1$ | | 4.2 |
| Morphine[a] | | 1.6 |

[a]The Merck Index, 9th Ed., 6108

TABLE 2

| | Spontaneous mouse-killing | |
|---|---|---|
| | | $ED_{50}$, mg/kg s.c. |
| Compound | R' | 1 hr | 2 hr |
| 1 | Et | 1.0 | 1.8 |
| 3 | cyclo-Pr | 2.6 | 3.7 |
| Amitriptyline[a] | | >10 | 6.4 |

TABLE 2-continued

| | | Spontaneous mouse-killing | |
|---|---|---|---|
| | | ED$_{50}$, mg/kg s.c. | |
| Compound | R' | 1 hr | 2 hr |
| B | | >10 | >10 |

$(a)$ The Merck Index, 9th Ed., 504

TABLE 3

| | Isolation-induced aggressive behaviour. | |
|---|---|---|
| Compound | R' | ED$_{50}$, mg/kg, s.c. |
| 1 | Et | 2.8 |
| 3 | cyclo-Pr | 1.4 |
| Chlorpromazine$(a)$ | | 1.4 |
| Amitriptyline$(b)$ | | 5 |
| Diazepam$(c)$ | | 6.7 |
| B | | 10 |

$(a)$ The Merck Index, 9th Ed., 2175
$(b)$ The Merck Index, 9th Ed., 504
$(c)$ The Merck Index, 9th Ed., 2961

The formula I bases are convertible to therapeutically active non-toxic acid addition salts by treatment with an appropriate acid, e.g. an inorganic acid, such as a hydrohalic acid, especially hydrochloric and hydrobromic acid, or sulfuric acid, nitric acid, phosphoric acid and the like, or an organic acid, such as acetic, propionic, glycolic, lactic, malonic, succinic, fumaric, tartaric, citric and the like acids. Conversely, the salt form can be converted by treatment with alkali into the free base form.

The compounds I of the invention are very stable in aquous solutions and other kinds of pharmaceutical formulations. Thus, the compounds are well suited for preparing sterile solutions.

Effective quantities of any of the foregoing pharmacologically active compounds of formula I may be administered to a human being or animal for therapeutic purposes according to usual routes of administration and in usual forms, such as orally in solutions, emulsions, suspensions, pills, tablets and capsules, in pharmaceutically acceptable carriers and parenterally in the form of sterile solutions. For the parenteral administration of the active substance the carrier or excipient may be a sterile, parenterally acceptable liquid, e.g. water, or a parenterally acceptable oil, e.g. arachidic oil.

Although very small quantities of the active materials of the present invention are effective when minor therapy is involved or in the cases of administration to subjects having a relatively low body weight, unit dosages are usually from 2 milligrams upwards preferably 25, 50 or 100 milligrams or even higher depending on the condition to be treated and the age and weight of the patient as well as the response to the medication.

The unit dose may be from 0.1 to 200 milligrams, preferably from 10 to 50 milligrams. Daily dosages should preferably range from 10 milligrams to 200 milligrams. The exact individual dosages as well as daily dosages will, of course, be determined according to standard medical principles under the direction of a physician or veterinarian.

The following formulations are representative for all of the pharmacologically active compounds of this invention. Example of a suitable capsule formulation:

| | per capsule, mg |
|---|---|
| Active ingredient, as salt | 10 |
| Lactose | 250 |
| Starch | 120 |
| Magnesium stearate | 5 |
| Total | 385 |

In case of higher amounts of active ingredient, the amount of lactose used may be reduced.

Example of a suitable tablet formulation:

| | per tablet, mg |
|---|---|
| Active ingredient, as salt | 10 |
| Potato starch | 90 |
| Colloidal silica | 10 |
| Talc | 20 |
| Magnesium stearate | 2 |
| 5% Aqueous solution of gelatin | 25 |
| Total | 157 |

The pharmaceutical preparations may also contain therapeutically useful substances other than the pharmacologically active compounds of formula I.

The following examples are intended to illustrate the present invention, without limiting the scope thereof.

EXAMPLE 1

1-Cyclohexanecarbonyl-4-benzylpiperazine

To a solution of 21.2 g (0.12 mole) of 1-benzylpiperazine in 100 ml of CHCl$_3$ was added dropwise over a period of 30 minutes a solution of 15.0 g (0.10 mole) of cyclohexanecarbonyl chloride in 50 ml of CHCl$_3$. The mixture was allowed to stand at room temperature during 45 minutes and was made basic with 5 g of sodium hydroxide in 50 ml of water. The nonaqueous layer was separated, dried over sodium sulphate and concentrated. The residue was distilled b.p. 150°–56° C. at 0.1–0.2 mmHg to give 21.2 g of 1-cyclohexanecarbonyl-4-benzylpiperazine.

EXAMPLE 2

1-Cyclohexanecarbonylpiperazine hydrochloride 14.3 g (0.05 mole) of 1-cyclohexanecarbonyl-4-benzylpiperazine dissolved in 250 ml of ethanol and acidified with conc. HCl was treated with hydrogen over a palladium catalyst at 1500 psi and 100° C. The catalyst was removed by filtration and the solvent removed under reduced pressure. The residue was dissolved in isopropanol. On short standing a white crystalline precipitate appeared which was collected by filtration to give 10.0 g of 1-cyclohexanecarbonylpiperazine hydrochloride.

EXAMPLE 3

1-Cyclohexanecarbonyl-4-[4,4-(di-p-fluorophenyl)-butyl]piperazine hydrochloride

To 7.0 g (0.03 mole) of 1-cyclohexanecarbonylpiperazine hydrochloride was added a solution of 1.5 g of sodium hydroxide in 50 ml of water. The mixture was extracted with CHCl$_3$. The combined extracts were dried over sodium sulphate and concentrated. The residue was dissolved in 10 ml of ethanol. 10.0 g (0.036 mole) of 4-chloro-1,1-(di-fluorophenyl)-butane and 5.0 g of sodium bicarbonate was added. The mixture was heated at reflux for 36 hours. 100 ml of water was added. The mixture was extracted twice with CHCl$_3$.

The combined extracts were dried over sodium sulphate and concentrated. The residue was dissolved in ethanol-ether and the hydrochloride was precipitated with ethanolic HCl. The solid was collected by filtration and recrystallised from 2-butanone to give 8.2 g of 1-cyclohexanecarbonyl-4-[4,4-(di-p-fluorophenyl)-butyl]piperazine hydrochloride. Melting point 156°-58° C.

EXAMPLE 4

1-Ethylcarbonyl-4-[4,4-(di-p-fluorophenyl)butyl]-piperazine hydrochloride

To a solution of 3.3 g (0.01 mole) of 1-[4,4-(di-p-fluorophenyl)butyl]piperazine in 15 ml of CHCl$_3$ was added dropwise over a period of 15 minutes 1.05 g (0.011 mole) of propionyl chloride in 15 ml of CHCl$_3$. The mixture was allowed to stand at room temperature during 1 hour and was made basic with 0.8 g of sodium hydroxide in 25 ml of water. The nonaqueous layer was separated, dried over sodium sulphate and concentrated.

The residual oil was dissolved in 2-butanone and the hydrochloride was precipitated with ethanolic HCl. The solid was collected by filtration and recrystallized from 2-butanone to give 3.2 g of 1-ethylcarbonyl-4-[4,4-(di-p-fluorophenyl)butyl]-piperazine hydrochloride. Melting point 171°-173° C.

TABLE IV

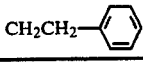

| Example | Method in accordance with example | R' | M.p.$^{(a)}$ °C. | Salt |
|---|---|---|---|---|
| 5 | 4 | n-C$_3$H$_7$ | 123–124 | HCl |
| 6 | 4 | iso-C$_3$H$_7$ | 156–158 | HCl |
| 7 | 4 | cyclo-C$_3$H$_5$ | 165–166 | HCl |
| 8 | 4 | n-C$_4$H$_9$ | 143–144 | HCl |
| 9 | 1 + 2 + 3 | tert-C$_4$H$_9$ | 174–175 | HCl |
| 10 | 4 | n-C$_7$H$_{15}$ | 120–121 | HCl |
| 11 | 4 |  | 191–192 | HCl |
| 12 | 4 | —Cl | 221–222 | HCl |
| 13 | 4 | CH$_2$— | 186–187 | HCl |
| 14 | 4 | CH$_2$CH$_2$— | 173–174 | HCl |

$^{(a)}$Melting points are uncorrected

What we claim is:

1. A compound having the formula:

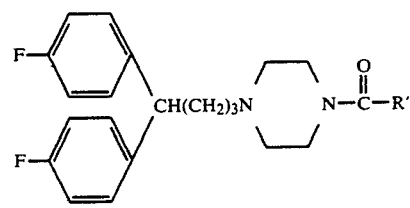

wherein R' is selected from the group consisting of alkyl straight or branch chained having from 2 to 10 carbon atoms, cycloalkyl having from 3 to 8 carbon atoms, aralkyl having from 7 to 9 carbon atoms, phenyl and substituted phenyl wherein the substituents of the substituted phenyl are selected from the group consisting of one to three F, Cl, Br, lower alkyl having from 1 to 5 carbon atoms, lower alkoxy having from 1 to 5 carbon atoms, alkylenedioxy having from 1 to 3 carbon atoms, —CF$_3$ and —CN and pharmaceutically acceptable salts thereof.

2. A compound of the formula

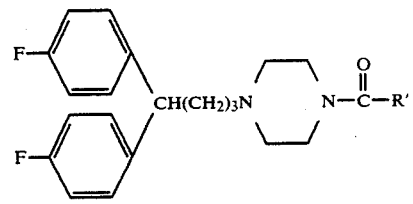

wherein R' is ethyl.

3. A compound of the formula

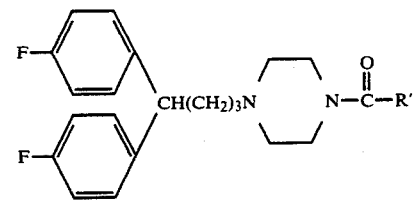

wherein R' is isopropyl.

4. A compound of the formula

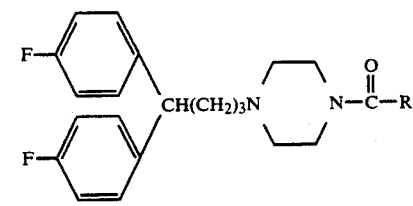

wherein R' is cyclopropyl.

5. A compound of the formula

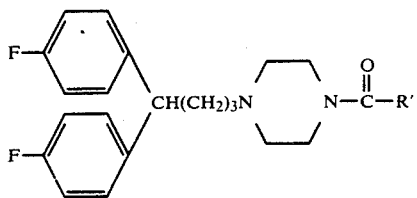

wherein R' is propyl.

6. A pharmaceutical composition characterized in that it contains a therapeutically effective amount of a compound of formula I as defined in claim 1 in combination with a conventional pharmaceutically acceptable carrier.

7. A method of treating mammals for anti-aggressive purposes comprising administrating an anti-aggressive effective amount of a compound of Formula I as defined in claim 1.

8. A method of treating mammals suffering from mental disorders comprising administrating a therapeutically effective amount of a compound of Formula I as defined in claim 1.

9. A method of treating mammals for analgetic purposes comprising administrating an analgetically effective amount of a compound of Formula I as defined in claim 1.

* * * * *